United States Patent
Schultheis et al.

(10) Patent No.: US 11,633,090 B2
(45) Date of Patent: Apr. 25, 2023

(54) ENDOSCOPE, DISPOSABLE ENDOSCOPE SYSTEM AND LIGHT SOURCE FOR ENDOSCOPE

(71) Applicant: SCHOTT AG, Mainz (DE)

(72) Inventors: Bernd Schultheis, Schwabenheim (DE); Martin Cramer, Wiesbaden (DE); Hubertus Russert, Jugenheim (DE); Holger Werner, Frankfurt (DE); Jens Vietor, Taunusstein (DE); Volker Hagemann, Nieder-Olm (DE); Jürgen Meinl, Hohenstein-Holzhausen (DE); Jonas Grimm, Bad Schwalbach (DE); Oliver Keiper, Hünstetten (DE)

(73) Assignee: SCHOTT AG, Mainz (DE)

( * ) Notice: Subject to any disclaimer, the term of this patent is extended or adjusted under 35 U.S.C. 154(b) by 11 days.

(21) Appl. No.: 17/112,886

(22) Filed: Dec. 4, 2020

(65) Prior Publication Data
US 2021/0169316 A1    Jun. 10, 2021

(30) Foreign Application Priority Data
Dec. 4, 2019  (DE) ...................... 10 2019 133 042.4

(51) Int. Cl.
*A61B 17/22*    (2006.01)
*A61B 1/06*    (2006.01)
(Continued)

(52) U.S. Cl.
CPC ........ *A61B 1/0638* (2013.01); *A61B 1/00105* (2013.01); *A61B 1/00144* (2013.01);
(Continued)

(58) Field of Classification Search
CPC .............. A61B 1/0638; A61B 1/00105; A61B 1/00144; A61B 1/05; A61B 1/063;
(Continued)

(56) References Cited

U.S. PATENT DOCUMENTS

| 3,581,738 A | 6/1971 | Moore |
| 4,783,135 A | 11/1988 | Utsumi |
(Continued)

FOREIGN PATENT DOCUMENTS

| DE | 1596485 | 7/1970 |
| DE | 3724749 | 2/1988 |
(Continued)

OTHER PUBLICATIONS

Hewak, "Fiber and guided wave optics—Fabrication of Optical Fiber", Encyclopedia of Modern Optics 2005, Abstract.
(Continued)

*Primary Examiner* — Howard D Brown, Jr.
(74) *Attorney, Agent, or Firm* — Ruggiero McAllister & McMahon LLC

(57) ABSTRACT

An endoscope is provided that includes a first component, a second component, a light source, an image capturing element, and a light guide. The second component has a proximal end and a distal end with proximal end coupled to the first component. The light source is integrated in the first component and includes a laser and a converter. The laser emits primary light and the converter converts the primary light at least partially into secondary light that has a different wavelength. The image capturing element is arranged at the distal end. The light guide has an optical fiber that extends through the second component. The converter is coupled to the proximal end such that the primary and secondary light is injected into the optical fiber, is conducted from the proximal end to the distal end, and emitted at the distal end.

25 Claims, 2 Drawing Sheets

(51) Int. Cl.
| | |
|---|---|
| *A61B 1/00* | (2006.01) |
| *A61B 1/05* | (2006.01) |
| *A61B 1/07* | (2006.01) |
| *G02B 6/02* | (2006.01) |
| *G02B 6/06* | (2006.01) |
| *H04N 5/225* | (2006.01) |

(52) U.S. Cl.
CPC ............. *A61B 1/05* (2013.01); *A61B 1/063* (2013.01); *A61B 1/07* (2013.01); *G02B 6/02395* (2013.01); *G02B 6/06* (2013.01); *H04N 5/2256* (2013.01); *H04N 2005/2255* (2013.01)

(58) Field of Classification Search
CPC ....... A61B 1/07; A61B 1/0653; A61B 1/0669; A61B 1/0684; A61B 1/04; A61B 1/00011; A61B 1/0676; G02B 6/02395; G02B 6/06; H04N 5/2256; H04N 2005/2255
See application file for complete search history.

(56) References Cited

U.S. PATENT DOCUMENTS

| | | | |
|---|---|---|---|
| 4,807,597 A | 2/1989 | Tsuno | |
| 4,867,529 A | 9/1989 | Utsumi | |
| 4,964,710 A | 10/1990 | Leiner | |
| 5,436,655 A | 7/1995 | Hiyama | |
| 5,704,899 A | 1/1998 | Milo | |
| 5,761,356 A | 6/1998 | Li | |
| 6,249,348 B1* | 6/2001 | Jung | G01J 3/027 250/226 |
| 6,398,721 B1 | 6/2002 | Kakamura | |
| 6,556,851 B1 | 4/2003 | Ott | |
| 10,393,957 B1 | 8/2019 | Potter | |
| 11,215,752 B1 | 1/2022 | Lin | |
| 2004/0246744 A1 | 12/2004 | Krupa | |
| 2005/0197623 A1 | 9/2005 | Leeflang | |
| 2006/0041193 A1* | 2/2006 | Wright | A61B 1/0684 600/179 |
| 2006/0069314 A1 | 3/2006 | Farr | |
| 2006/0072893 A1 | 4/2006 | Wied | |
| 2006/0152926 A1 | 7/2006 | Hama | |
| 2006/0279950 A1 | 12/2006 | Hama | |
| 2007/0249907 A1 | 10/2007 | Boulais | |
| 2008/0013900 A1 | 1/2008 | Harris | |
| 2008/0142828 A1 | 6/2008 | Yang | |
| 2008/0300456 A1 | 12/2008 | Irion | |
| 2009/0163342 A1 | 6/2009 | Kolberg | |
| 2009/0312607 A1 | 12/2009 | Sunagawa | |
| 2009/0321348 A1 | 12/2009 | Hoermann | |
| 2010/0010314 A1 | 1/2010 | Krattiger | |
| 2010/0046897 A1 | 2/2010 | Toriya | |
| 2011/0182552 A1 | 7/2011 | Russert | |
| 2011/0282160 A1 | 11/2011 | Bhadri | |
| 2012/0010465 A1* | 1/2012 | Erikawa | A61B 1/0653 600/109 |
| 2012/0289779 A1 | 11/2012 | Kinoshita | |
| 2013/0175720 A1 | 7/2013 | Otsuka | |
| 2013/0342110 A1* | 12/2013 | Yamamoto | A61B 1/00165 315/151 |
| 2014/0107630 A1 | 4/2014 | Yeik | |
| 2014/0221749 A1 | 8/2014 | Grant | |
| 2014/0303551 A1* | 10/2014 | Germain | A61B 17/42 606/115 |
| 2014/0350343 A1* | 11/2014 | Kim | G02B 6/262 600/121 |
| 2014/0376868 A1 | 12/2014 | Ritter | |
| 2015/0016140 A1 | 1/2015 | Weingaertner | |
| 2015/0049994 A1* | 2/2015 | Schultheis | G02B 6/443 385/100 |
| 2015/0216418 A1* | 8/2015 | Ammon | A61B 1/24 433/29 |
| 2015/0374217 A1* | 12/2015 | Sinofsky | F21K 2/00 600/177 |
| 2016/0022119 A1 | 1/2016 | Shahmoon | |
| 2016/0227985 A1 | 8/2016 | Ikeda | |
| 2016/0334616 A1 | 11/2016 | Vayser | |
| 2017/0003164 A1* | 1/2017 | Tanaka | G02B 23/2469 |
| 2017/0052319 A1 | 2/2017 | Schultheis | |
| 2017/0231477 A1 | 8/2017 | Del Nido | |
| 2017/0231698 A1 | 8/2017 | Goldfarb | |
| 2018/0055342 A1 | 3/2018 | Sakai | |
| 2018/0228354 A1 | 8/2018 | Yabe | |
| 2019/0014979 A1 | 1/2019 | Czupalla | |
| 2019/0270667 A1 | 9/2019 | Sumita | |
| 2019/0290100 A1 | 9/2019 | Ramachandran | |
| 2019/0346649 A1 | 11/2019 | Tanaka | |
| 2019/0374095 A1 | 12/2019 | Lord | |
| 2020/0178781 A1* | 6/2020 | Tabata | A61B 1/06 |
| 2020/0222712 A1 | 7/2020 | Schultheis | |
| 2020/0253592 A1 | 8/2020 | Popejoy | |
| 2020/0301064 A1 | 9/2020 | Kojima | |
| 2021/0022588 A1 | 1/2021 | Schultheis | |
| 2021/0093170 A1 | 4/2021 | Schultheis | |
| 2021/0145257 A1 | 5/2021 | Levinson | |
| 2021/0282631 A1* | 9/2021 | Schultheis | A61B 1/0669 |

FOREIGN PATENT DOCUMENTS

| | | |
|---|---|---|
| DE | 69720736 | 3/2004 |
| DE | 102004048741 | 5/2006 |
| DE | 102006053487 | 5/2008 |
| DE | 102006040214 | 7/2008 |
| DE | 102007026234 | 12/2008 |
| DE | 102008044938 | 3/2010 |
| DE | 102009004159 | 7/2010 |
| DE | 102011114575 | 4/2013 |
| DE | 102012100233 | 5/2014 |
| DE | 102013208838 | 11/2014 |
| DE | 102011119972 | 10/2015 |
| DE | 102014208756 | 11/2015 |
| DE | 102015015041 | 5/2017 |
| DE | 102017108698 | 10/2018 |
| DE | 102017122756 | 4/2019 |
| DE | 102018107523 | 10/2019 |
| DE | 102019125912 | 4/2021 |
| EP | 1890173 | 2/2008 |
| EP | 2072477 | 3/2010 |
| EP | 3097845 | 11/2016 |
| GB | 1242883 | 8/1971 |
| JP | S61143120 | 9/1986 |
| JP | S63151918 | 6/1988 |
| JP | H10258022 | 9/1998 |
| JP | 2000079089 | 3/2000 |
| JP | 2002531846 | 9/2002 |
| JP | 2003290135 | 10/2003 |
| JP | 2009018081 | 1/2009 |
| JP | 2015228887 | 12/2015 |
| JP | 2017524505 | 8/2017 |
| JP | 2017195960 | 11/2017 |
| WO | 3912479 | 12/1989 |
| WO | 2013092498 | 6/2013 |
| WO | 2016185537 | 11/2016 |

OTHER PUBLICATIONS

EN 60601-1, 3rd edition, table 3.
European Medical Device Directive MDD 93/42 EEC.
DIN EN ISO 10993, Fifth Edition, Aug. 2018.
Regulation (EU) 2017/745 of Apr. 5, 2017.
English translation of DIN EN ISO 10993-1: Apr. 2010.
DIN EN ISO 10993-5, "Biological evaluation of medical devices—Part 5: Tests for in vitro cytotoxicity (ISO 10993-5:2009) English version of DIN EN ISO 10993-5:2009-10", Oct. 2009, 44 pages.

* cited by examiner

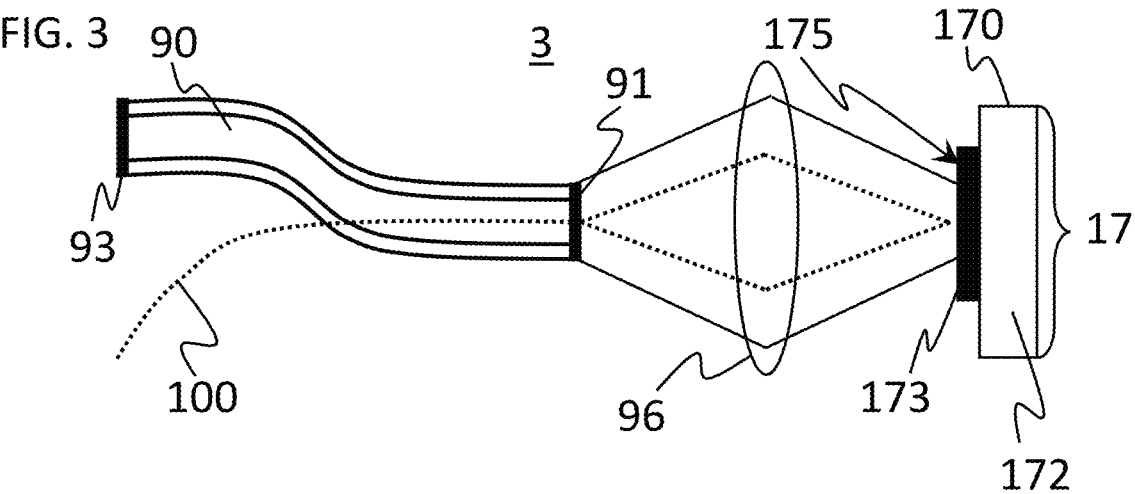
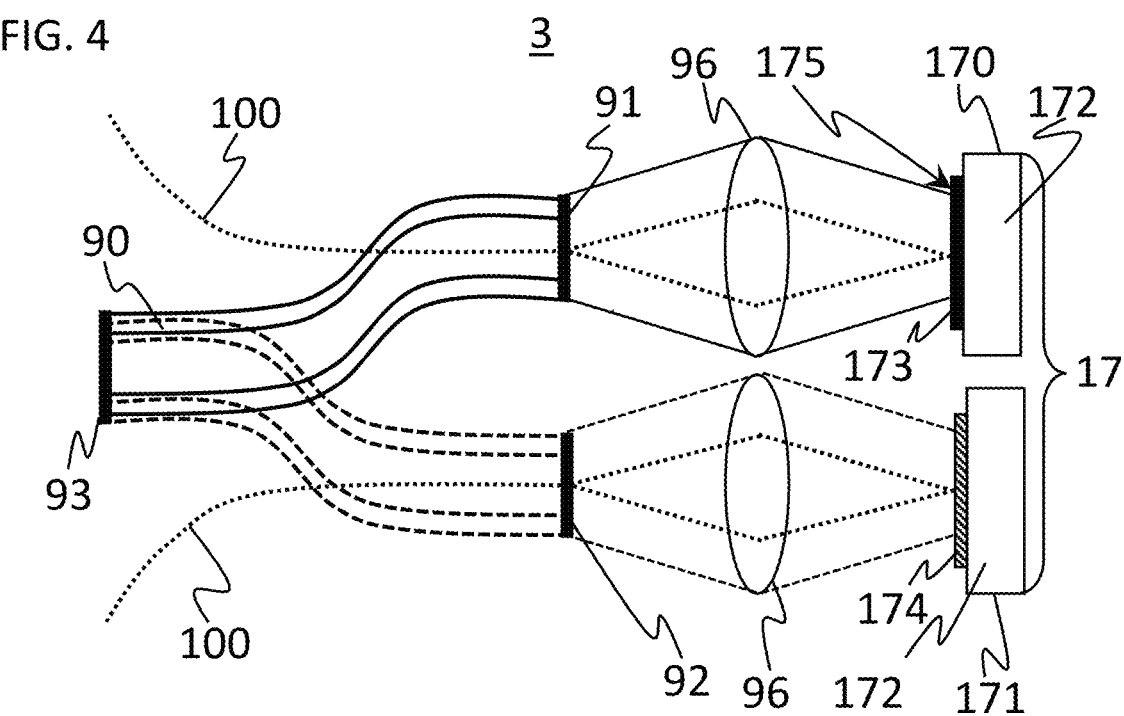

ENDOSCOPE, DISPOSABLE ENDOSCOPE SYSTEM AND LIGHT SOURCE FOR ENDOSCOPE

CROSS REFERENCE TO RELATED APPLICATIONS

This application claims benefit under 35 USC § 119 of German Application 10 2019 133 042.4 filed Dec. 4, 2019, the entire contents of which are incorporated herein by reference.

BACKGROUND

1. Field of the Invention

The invention generally relates to endoscopes and endoscope systems, more particularly to disposable endoscopes and/or disposable endoscope systems. Another aspect relates to a light source for an endoscope and/or for an endoscope system such as a disposable endoscope and/or a disposable endoscope system.

2. Description of Related Art

Diagnostic, surgical, and/or therapeutic devices such as endoscopes for diagnosis, for minimally invasive interventions, or for therapy are known to have rigid or flexible designs and have been sufficiently described in the literature. Nowadays, disposable endoscope are increasingly being used, in particular to increase patient safety during medical examinations, therapies and/or minimally invasive interventions, since single use allows to prevent contamination. In fact, prior art endoscopes have been designed so as to be reprocessable in terms of medical technology, i.e. they can be cleaned, sterilized and, above all, they are autoclavable.

Nevertheless, it may occasionally happen, due to incorrect application of reprocessing or unfavorable design of such devices, that the necessary reduction in the number of bacteria fails to be achieved and hence bacteria may be transferred to the patient during the next application. This can be prevented by using such disposable endoscopes.

Another aspect for the increased use of disposable endoscopes is economic assessment. In particular the reprocessing process that has to be carried out properly and regularly after each treatment implies high costs for the practicing doctor or the clinic nowadays. Moreover, high investments are required for purifying devices such as thermal disinfectors and autoclave devices and/or plasma sterilization devices, so that, overall, the use of such disposable endoscopes is justified.

Another advantage results from the fact that such disposable endoscopes can be used as transportable hand-held devices and can therefore also be employed in emergency medicine, in military emergency missions or in regions that are difficult to access, for example during disaster relief missions, where in particular reprocessing options are not available.

Such disposable endoscopes, also known as single-use endoscopes, as described in the literature have been described in the following documents.

Document U.S. Pat. No. 3,581,738 A1 discloses a disposable endoscope comprising a body of synthetic resinous material having a generally tubular side wall defining a speculum and a unitary elongated light-conducting member embedded in the side wall, the member being formed of a light-conducting material clad with a transparent material having an index of refraction different from that of the light-conducting material, the body being formed of two mating halves divided axially of the endoscope, each half having a member-enclosing wall.

Document U.S. Pat. No. 4,964,710 A1 describes a rigid endoscope equipped with an objective lens system, an ocular lens and an intermediate relay lens. The relay system is a hybrid system that uses both plastic and glass components. The plastic components comprise an even number (N) of axially aligned lenses, each having a length which is of the order of their diameter. The glass components comprise an odd number (N minus 1) of axially aligned plano glass cylinders with polished end faces.

Document EP 1890173 A1 discloses a method for producing an optical light guide that can be used in such endoscopes. A plurality of optical fibers are bundled, and the fiber bundle is cut at a part of a mouthpiece which is fixed to an intermediate part of the fiber bundle. Thus, the fiber bundle is divided into a first optical fiber bundle and a second optical fiber bundle. Separation surfaces of the first and second optical fiber bundles have the same properties and condition since the first and second optical fiber bundles are formed of the fiber bundle that is obtained by bundling the same optical fibers. The first optical fiber bundle is assembled in an insertion section of an endoscope and the second optical fiber bundle is assembled in a flexible tube, whereby a first light guide is formed in the insertion section of the endoscope and a second light guide is formed in the flexible tube. Thereby, a separable light transmission path of the light guide is formed.

Since such endoscopes are subject to high cost pressure due to their single use, the assemblies and components have to be producible in a cost-effective way. Among the main components for imaging and illumination are light guides or image guides, and these are currently still assembled and processed in rather complex processing steps. What makes the current light guides or image guides comparatively expensive is often due to complex mechanical components partly combined with optical elements such as lenses that form part of such light guides or image guides, and sometimes complex processing steps such as grinding and polishing of the end faces are moreover involved.

On the other hand, particular lighting requirements must also be taken into account when using endoscopes, especially in medical technology. In addition to transmitting the light provided by a light source to the examination site in the best possible loss-free manner, this includes a true-to-color or an intentionally colored representation of the examination site and also the avoiding of introducing unnecessary heat to the examination site. A particular challenge lies in the luminous flux provided by the light source as well as the transmission of the light to the distal end of an endoscope. Especially endoscope systems with a small diameter require extremely bright light sources on the one hand and luminous flux-optimized light guides on the other.

If active electronic components are used, such as camera chips and/or LEDs for lighting, it is moreover necessary to take into account requirements with regard to electrical insulation, electrical shielding and patient leakage currents, which must not exceed maximum threshold values, depending on the field of application of the endoscope. For applications at the heart, for example, a maximum leakage current of 10 µA is required, corresponding to CF classification (see EN 60601-1, $3^{rd}$ edition, tab. 3).

In addition to these illumination-related and electrical requirements, requirements regarding biocompatibility must also be observed. For biocompatibility it is necessary to ensure that the material is compatible with the human organism. For medical devices that might come into contact with the human body, regulatory requirements request to determine and assess possible interactions and undesirable side effects. The selection of the required tests depends on the type of contact and duration of contact in the human body. According to European Medical Device Directive MDD 93/42 EEC (MDD for short) and Regulation (EU) 2017/745 of Apr. 5, 2017 (MDR for short), this biological assessment of a product is always necessary if there is direct contact between the material or product and the patient.

The main standards for biological tests and evaluation of materials are DIN EN ISO 10993 and the test according to United States Pharmacopeia Class VI (USP Class VI). Although the much more extensive ISO 10993 was originally intended to replace the test according to USP Class VI, the USP test is used very frequently today in particular for evaluating biocompatible plastics. For this purpose, the materials intended for invasive application are evaluated with regard to their chemical compounds on the one hand, and are on the other hand subjected to a cytotoxicity test in which possible toxic effects to living cell cultures are examined. The requirements for this are summarized in DIN EN ISO 10993, especially in parts-1 and -5 (DIN EN ISO 10993-1: 2010-04). In the United States, this is subject to FDA requirements. The requirements corresponding to DIN EN ISO 10993 are specified in USP Class VI there.

Another advantage of the endoscopes in the form of single-use endoscopes is that they do not require to take into account the known reprocessing methods in the form of cleaning or disinfection processes involving strongly basic solutions and sterilization by autoclaving at temperatures of up to 135° C. and typical steam pressures of about 3 bar, which in particular permits to choose more cost-effective materials. The only thing that needs to be considered for the materials is their suitability for gas sterilization processes, such as ethylene oxide sterilization, and the RoHS (Restriction of Hazardous Substances) and REACH (Registration, Evaluation, Authorisation and Restriction of Chemicals) regulations.

The Applicant's own applications DE 10 2019 125 912 and DE 10 2018 107 523 relate to various aspects of light guides. A laser-based light source is not mentioned.

U.S. Pat. No. 6,398,721 B relates to a surgical microscopy device which may comprise a laser diode.

U.S. patent application US 2006/0279950 A1 discloses an LED. Endoscopes are not mentioned, but light guides comprising fibers can be used, for example. The LED is operated in transmission.

U.S. patent application US 2006/0152926 A1 also describes an LED which may also be used in endoscopes by way of example. The LED is operated in transmission.

U.S. Pat. No. 5,436,655 A describes an endoscope which may comprise a laser.

A highly efficient light source is described in U.S. patent application US 2004/0246744 A1.

U.S. patent application US 2019/0014979 A1 describes an endoscope which can also be operated with laser light.

U.S. patent application US 2019/0290100 A1 describes an optical imaging system which can be used in particular in fluorescence microscopy (STED microscopy).

International patent application WO 2013/092498 A1 discloses an endoscope that may include laser diodes as light sources.

U.S. patent application US 2006/0069314 A1 describes a solid-state light source for an endoscope.

German patent application DE 10 2017 108 698 A1 discloses an optoelectronic component.

However, it has not yet been possible to exploit the advantages of high luminance lighting in a cost-effective way. In particular it is currently not possible to exploit the advantages of laser light for disposable endoscopes.

SUMMARY

The object of the invention is to at least partially overcome or at least mitigate the deficiencies of the prior art, and in particular to provide endoscope systems which comprise a bright light source or lighting with high brightness in particular for single-use applications, and an light guiding system optimized for this purpose.

The invention therefore relates to an endoscope comprising a first component and a second component, with a light source integrated in the first component, the second component having a proximal end that is coupled to the first component, preferably a detachably coupled proximal end, and a distal end; and an element for image capturing or transmission and/or for capturing or transmission of optical information such as a camera chip or a fiber optic element arranged at the distal end; and a light guide comprising at least one optical fiber extending through the second component to conduct light of the light source from the proximal end to the distal end and to emit it at the distal end; and preferably a power supply line for electrically powering the camera chip, in particular if such a camera chip is provided at the distal end; and wherein the light source comprises at least one laser for emitting primary light, and a converter that converts the light from the laser at least partially into light of a different wavelength (secondary light) and emits this light; wherein the converter is coupled to the proximal end of the second component coupled to the first component such that the light converted and emitted by the converter is injected into the light guide. Fiber optic elements for image capturing or image transfer are also known as "image guides" and consist of some tens of thousands of individual fibers arranged in a mutually ordered manner on the end faces. Such fiber-optic elements may in particular be made of glass or of plastics or may comprise glass or plastics, for example in the form of glass optical fibers or plastic optical fibers.

Such a configuration of an endoscope has a number of advantages.

According to the present disclosure, the endoscope is divided into two components. The first component which may also be referred to as the proximal component has a light source integrated therein, which comprises at least one laser adapted to emit primary light. For example, the laser may be configured so as to emit blue and/or ultraviolet light. The first component furthermore comprises a converter that is designed to convert the light of the laser at least partially into light of a different wavelength and to emit it.

This is advantageous because it allows to use laser light. In particular, it is possible to achieve particularly high illumination intensity in this way.

The converter is coupled to the proximal end of the second component, which in turn is coupled to the first component, so that the light converted and emitted by the converter is or can be injected into the light guide.

In other words, the first component is designed so as to be connectable to a second component which may also be referred to as a distal component, or it may even be provided in a form connected to the second component.

Depending on the precise configuration and depending on the type of elements it consists of, the first component may be provided in the form of a handpiece, for example, that is to say as a component that also serves to manipulate and/or hold the endoscope, for example. However, it is also possible that the first component comprises elements which serve to control and/or operate an endoscope, for example in the form of a control and/or evaluation unit, so that in this case the first component may also be configured as an operating device for the endoscope.

Furthermore, the endoscope comprises a second component, which has a proximal end and a distal end and a light guide comprising at least one optical fiber extending through the second component. The light guide is adapted to conduct light of the light source from the proximal end to the distal end and to emit it at the distal end. An image capturing element such as a camera chip for image capturing or a fiber optic image guide is arranged at the distal end. Furthermore, if the distal end comprises a camera chip, the second component preferably comprises a power supply line for electrically powering the camera chip.

Such a configuration of the endoscope with two components (or assemblies) is advantageous. This is because according to the described implementation the endoscope is configured so that the first component includes elements such as the light source comprising at least one laser, which are rather expensive, while the second component, on the other hand, comprises elements that are relatively inexpensive. It is therefore possible to decouple the endoscope, and in this way inexpensive elements can be accommodated in a comparatively cost-effective single-use assembly, for example, whereas the less cost-effective expensive elements are accommodated in a multi-use assembly.

This now makes it possible for the first time to provide an endoscope that combines the advantages of very high-quality lighting with the advantages of an endoscope that is only intended for single use, for example. It should be noted that the endoscope according to the present disclosure does not necessarily have to be designed as a single-use endoscope or at least partially as a single-use endoscope. Rather, it is also conceivable to adapt this according to requirements.

However, it can be advantageous if the first component and the second component are coupled to one another so as to be detachable from one another. If the endoscope is designed as an endoscope that is at least partially intended for single use, the second component can be disposed of after use, for example. However, it is also possible that the second component is detachably coupled to the first component, while nevertheless being intended for multiple use and, after having been separated from the first component, is subjected to particular cleaning and sterilization processes designated for medical use.

The endoscope according to the present disclosure, which can also be described as a modular endoscope, therefore also offers the possibility of simplified manipulation on the one hand. On the other hand, high-quality lighting can be combined with the advantages of a single-use device, such as lighting by a laser, which provides for high light intensity, especially if the endoscope is a disposable endoscope or an endoscope at least partially designed as a disposable endoscope, i.e. an endoscope comprising at least some components that are intended for single use only.

The second component that includes a light guide may be rigid, for example, or else may be flexible. More generally, the second component can be understood as what is known as an endoscope shaft, and in the context of the present disclosure "shaft" is generally understood to mean both a rigid second component and a flexible component which, for example, merely comprises a flexible outer sheathing tube made of a polymer material, for example. If the second component is rigid, it may be designed such that, for example, the light guide forming part of the second component is at least partially surrounded by a tube section or by several tube sections made of a metal or a plastic. The exact design of the second component can be selected depending on the preferred field of application of the endoscope.

According to a preferred embodiment, the converter comprises a ceramic converter material. Such a configuration is advantageous because it provides for particularly high light intensity, even for white light. This is because ceramic converter materials are particularly heat-resistant, so that they allow to achieve particularly high luminance levels. Organically based converters or combinations of organic and ceramic converter materials are likewise conceivable. In particular, it is possible for the converter to be designed so as to comprise a converter element which includes two or more converter materials that are in particular adapted so as to convert primary light into light of different spectral compositions. For example, it is conceivable that a converter element comprises a so-called "yellow" phosphor and a so-called "red" phosphor. For example, these materials can be provided as a mixture, for example a mixture comprising an organic material and a ceramic material, or as a mixture of organic or ceramic materials. However, the converter may as well be designed so as to comprise a plurality of converter elements, each one comprising a different converter material. Combinations of these designs are conceivable as well.

In particular, the ceramic converter material may be made of or may comprise a luminescent ceramic material. In the context of the present disclosure this means that the converter may consist predominantly, that is to say at least of 50 wt %, or even essentially, that is to say at least of 90 wt % of a luminescent ceramic material, for example. It is also possible for the converter to consist entirely of the luminescent ceramic material. Thus, the converter and/or the converter element in particular comprises or consists of a luminescent ceramic material. The converter and/or the converter element may also be designed as a composite material, for example in the form of a phosphor-glass composite, or a phosphor-plastic composite, in particular a phosphor-silicone composite, or a phosphor-ceramic composite, and in this case it preferably comprises at least 10 wt % of a luminescent ceramic material, for example between 10 wt % and 30 wt %, in particular between 10 wt % and 20 wt %.

According to one embodiment, the converter and/or the converter element comprises a garnet-type ceramic material as the luminescent ceramic material, or consists predominantly thereof, i.e. at least of 50 wt %, or essentially, i.e. at least of 90 wt %, or is made entirely thereof, and the garnet-type ceramic material preferably has the following empirical formula:

$$A_3B_5O_{12}:RE, \text{ where}$$

A is Y and/or Gd and/or Lu, and

B is Al and/or Ga, and wherein RE is selected from the group of rare earth elements and preferably comprises Ce and/or Pr.

According to yet another embodiment, the garnet-type ceramic material has the following empirical formula:

$$(Y_{1-x}Ce_x)_3Al_5O_{12} \text{ and/or}$$

$$(Y_{1-x-y}Gd_yCe_x)_3Al_5O_{12} \text{ and/or}$$

$(Lu_{1-x}Ce_x)_3Al_5O_{12}$ and/or $(Y_{1-x-z}Lu_zCe_x)_3Al_5O_{12}$;

with the following applying for x: $0.005<x<0.05$; and for y: $0<y<0.2$; and for z: $0<z<1$.

According to one embodiment, the converter and/or the converter element comprises a luminescent ceramic material or consists predominantly thereof, i.e. at least 50 wt %, or essentially, i.e. at least 90 wt %, or entirely, wherein the converter is provided in the form of: a single-phase solid ceramic (known as optoceramic), and/or a multi-phase solid ceramic, and/or a single-phase or multi-phase ceramic exhibiting a particular porosity, and/or a composite material such as a phosphor-in-glass composite (PIG) and/or a phosphor-in-silicone composite (PIS).

According to a further embodiment, the ceramic material moreover includes other oxidic compounds (besides garnet compounds) and also nitridic compounds, in particular from the group of aluminum oxynitrides and silicon aluminum oxynitrides.

According to a further embodiment, the converter and/or the converter element is provided in the form of a porous sintered ceramic, the porosity being between 0.5% and 10%, preferably between 4% and 8%. The porosity is based on the volume here. The mean pore size is preferably between 400 µm and 1200 µm, more preferably between 600 µm and 1000 µm, and most preferably between 600 µm and 800 µm.

In the context of the present disclosure, single-phase ceramic (or optoceramic) is understood to mean that at least 95 vol % of the crystals and/or crystallites making up the ceramic are of the same crystal phase. Preferably, the percentage by volume of foreign phases is significantly lower. In particular, even more than 96 vol % or more than 97 vol % or more than 98 vol % or even more than 99 vol % of the crystals and/or crystallites making up the ceramic may form the same crystal phase. It is also not ruled out that a single-phase ceramic may furthermore contain amorphous components. However, these usually amount to less than 5 vol %.

It can be particularly advantageous if the ceramic material is designed so that the material has a thermal conductivity in the range from 1 W/mK to 20 W/mK. This provides for particularly good dissipation of the thermal energy that is being produced or has been produced during the conversion, so that the conversion properties of the converter material will alter only slightly, if at all, during the operation of the material.

The ceramic converter material may in particular be polycrystalline.

It is particularly advantageous if the material is provided in a homogeneous or essentially homogeneous form, homogeneous form of the material preferably meaning that the material is provided as a single-phase ceramic (or optoceramic).

According to a further embodiment, the converter comprises at least two ceramic converter materials which convert the laser light into light of different spectral compositions. Such an embodiment may in particular be advantageous if particularly precise and/or detailed examinations are required to determine the condition of the feature or area being examined, especially in the medical field when precise information about the condition of the tissue being examined is required, for example in order to be able to create targeted treatment and/or therapy plans. This is because it is possible in this way to achieve high illumination intensity and to obtain light with a composition deviating from "white" color coordinates, for example, and/or to adapt the spectral composition of the light on a case-by-case basis.

Particularly advantageously, the converter comprises two converter elements, with each of the converter elements comprising one of the ceramic converter materials, so that the converter elements convert the light into light of different spectral composition. In this way, a particularly straightforward adjustment of the color coordinates is achieved, in particular such a configuration allows particularly easily to illuminate only one of the two converter materials and/or to selectively distribute the laser light to the two converter materials through appropriate controlling.

According to one embodiment, the converter is optically coupled to the light guide in such a way that light remitted by the converter is injected or at least can be injected into the light guide. This is advantageous in order to ensure that light with just the desired spectral distribution is conducted through the light guide and onto the area to be examined by means of the endoscope. In the context of the present disclosure, remitted light is understood to mean light which is converted and/or scattered and/or reflected by the converter, unless expressly stated otherwise.

According to a further preferred embodiment, the laser is arranged and oriented towards the converter such that only light converted and/or scattered and/or reflected by the converter is injected into the light guide, which light may also include components of scattered or reflected primary light, for example.

Such a configuration of the endoscope is particularly advantageous from a safety point of view, since it prevents laser light from reaching the area to be examined.

It is generally possible for the converter and the laser to be arranged in what is known as a transmission configuration, so that the light from the laser passes through the converter, i.e. is transmitted, and thereby is converted and/or scattered. However, it is also possible and may even be preferable for the converter and the laser to be arranged in a reflection configuration, meaning that the laser light is incident on and reflected by the converter thereby being converted and/or scattered, in particular in order to ensure that no laser light, i.e. non-converted and/or non-scattered light as emitted by the laser reaches the area to be examined.

According to a further embodiment, the laser is arranged in such a way that the light from the laser is directed and/or can be directed in a direction substantially opposite to the light emission direction of the light converted and/or scattered and/or reflected by the converter and injected into the light guide. Especially such a configuration may be particularly advantageous from a safety point of view in order to prevent direct laser light from being injected into the light guide. Such a configuration of the endoscope may be implemented, for example, by providing the endoscope with a means that is used to direct the light from the laser in counter direction to the light emission direction of the light remitted by the converter, as stated above. For example, this means may be and/or comprise an optical fiber.

Here, an irradiation direction substantially opposite to the light emission direction of the light converted by the converter and injected into the light guide is understood to mean that an angle of at least ±10° is enclosed between the normal vector of the surface of the converter and/or the converter element(s) and the irradiation direction of the primary light.

Light guides suitable for such endoscope systems may, for example, comprise some tens, some hundreds up to a few thousands of individual fibers, and the exact number of individual fibers included in the light guide depends on the addressed end diameter of the light guide and/or on the diameter of the individual fibers making up the light guide, for example. Usual fiber diameters range between 20 µm and 100 µm. Typical diameters are 30 µm, 50 µm, and 70 µm.

In particular for single-use endoscopes or for endoscope systems with small dimensions it may be advantageous to use a few thick fibers as the optical fibers in order to ensure sufficient luminance or illumination intensity in the area to be examined. On the one hand, this allows for cost-effective rapid assembly and, on the other hand, it ensures a high luminous flux emanating from the laser light source toward the distal end of the endoscope.

A number of not more than twenty of such individual fibers, preferably not more than ten of such individual fibers has been found to be advantageous and a good tradeoff between assembly cost and sufficient luminous flux transmission, although a single fiber may already be sufficient for extremely thin endoscope systems. Bundles made up of three or seven individual fibers offer the advantage that they can be packed very tightly in a common sheathing. The 7-fiber assembly has the particular advantage that a rather circular arrangement of the individual fibers can be achieved in the common sheathing and that a packing density ideal for fibers of circular cross section is resulting. With such a 7-fiber assembly it is then possible, for example, to distribute the individual fibers around the camera chip or around the image conductor at the distal end of the endoscope in such a way that uniform illumination of the tissue to be examined can be achieved. However, given the quite common square shape of laser chips or light emitting diode chips or of the converter as the light source, it may also be advantageous to use four individual fibers or integer multiples of four or else two of such fibers. On the one hand, with regard to the highest possible active fiber area, i.e. the actual light-conducting cross-sectional area of the fiber, the cavities available for lighting purposes can be filled with more fibers, and on the other hand, better light injection can be achieved.

It has been found to be advantageous for the one optical fiber or the plurality of optical fibers to have a diameter ranging from 100 µm to 1000 µm, preferably up to 600 µm, more preferably ranging from 150 µm to 400 µm. Fibers of this type are much more easily assembled as individual fibers and still have a sufficiently small minimum bending radius. For today's endoscopes with a camera chip of 1×1 mm², for example, four individual fibers, one on each side of the camera, with a diameter ranging from 200 µm to 300 µm would be ideal. Arrangements with a total of eight or twelve individual fibers, i.e. two or three fibers on each side of the camera, are preferred as well, and in this case the individual fibers will have a diameter ranging from 150 µm to 200 µm at most. It may also be suggested, for example, to use fibers with different diameters in order to allow the area or the available space between the camera chip and the surrounding sheathing to be filled in the closest possible way so that the highest possible luminous flux can be achieved. With a 12-fiber arrangement, i.e. three fibers on each camera side, the fiber in the middle could for instance have a diameter of about 250 µm, while the other two fibers only have a diameter between 100 µm and 150 µm.

Instead of the individual fibers, it is in principle also possible to use thin fiber bundles which in particular consist of very thin individual fibers with an individual fiber diameter of preferably less than 70 µm, most preferably less than 50 µm, usually 30 µm, and which only have an extremely thin jacket that holds the fiber bundle together. Such fiber bundle designs are described in a not yet published parallel application of the present Applicant.

According to a further embodiment, the one optical fiber or the plurality of optical fibers are step-index glass fibers. Preferably, the one or more optical fibers are step-index glass fibers made of a glass composition that is free of lead and/or other heavy metals and free of antimony and/or arsenic and/or other critical elements such as Cr(VI), except for unavoidable traces.

In the context of the present disclosure, a fiber is understood to mean a body having a largest lateral dimension in one spatial direction of a Cartesian coordinate system that is larger than in the other two spatial directions perpendicular to this first spatial direction by at least a factor of 10, preferably by at least a factor of 50. In other words, a fiber is a very long, thin body.

In the context of the present disclosure, a step-index glass fiber is understood to mean a glass fiber having a refractive index that changes from the center, i.e. the core, outwards, in the form of at least one step. The glass fiber comprises a core glass and a cladding glass, the core glass having a different refractive index than the cladding glass.

A glass optical fiber comprises glass. Besides the glassy material, the glass optical fiber may furthermore comprise a further material at least partially enclosing the surface of the glassy material, which is known as surface sizing. Depending on the intended use, different glassy materials can be used for a glass optical fiber. In particular, the glass fiber may comprise a one-component and/or a multi-component glass. For example, the glass optical fiber may comprise fused silica as a substantially one-component glass and/or may in particular be in the form of a fused silica optical fiber, and the fused silica may also be doped, for example doped with OH ions and/or doped with fluorine, and/or may be provided in the form of water-rich or water-poor fused silica variations, for example, which will still be referred to as a one-component glass, or may comprise a multi-component glass, for example a multi-component silicate glass. Furthermore, the glass may also be in the form of a chalcogenide glass. Fused silica optical fiber or fused silica fiber also refers to a fiber comprising doped fused silica.

The optical fiber preferably comprises a fiber core and a fiber perimeter or fiber cladding layer. In preferred embodiments, the core layer is made of a core glass.

The optical fiber preferably comprises a fiber cladding surrounding the fiber core. In preferred embodiments, the fiber cladding comprises a cladding glass.

The fiber cladding preferably has a content of halogens or halides of less than 500 ppm (m/m), more preferably less than 400 ppm (m/m), yet more preferably less than 300 ppm (m/m), yet more preferably less than 250 ppm (m/m), yet more preferably less than 200 ppm (m/m), yet more preferably less than 150 ppm (m/m), yet more preferably less than 100 ppm (m/m), yet more preferably less than 80 ppm (m/m), yet more preferably less than 60 ppm (m/m), yet more preferably less than 40 ppm (m/m), yet more preferably less than 20 ppm (m/m), most preferably less than 10 ppm (m/m). In particularly preferred embodiments, the fiber cladding is free of halogens. Halogens include chlorine, fluorine, bromine, and/or iodine, or their anions, for example. An excessive concentration of halogens in the fiber cladding will lead to a formation of the corresponding halogen acids, in particular during steam sterilization, for example. Such halogen acids may reduce the resistance of the optical fiber article and may also be released therefrom. The halogen acids in particular attack materials such as stainless steel of autoclaves and endoscopes and cause the formation of undesirable rust.

The fiber core preferably has a content of halogens or halides of less than 500 ppm (m/m), more preferably less than 400 ppm (m/m), yet more preferably less than 300 ppm (m/m), yet more preferably less than 250 ppm (m/m), yet more preferably less than 200 ppm (m/m), yet more preferably less than 150 ppm (m/m), yet more preferably less than 100 ppm (m/m), yet more preferably less than 80 ppm (m/m), yet more preferably less than 60 ppm (m/m), yet more preferably less than 40 ppm (m/m), yet more preferably less than 20 ppm (m/m), most preferably less than 10 ppm (m/m). In particularly preferred embodiments, the core layer is free of halogens. Halogens according to the invention include chlorine, fluorine, bromine, and/or iodine, or their anions, for example. An excessive concentration of halogens in the fiber core will lead to a formation of the corresponding halogen acids, in particular during steam sterilization, for example. Such halogen acids may reduce the resistance of the optical fiber article and may also be released therefrom. The halogen acids in particular attack materials such as stainless steel of autoclaves and endoscopes and cause the formation of undesirable rust.

In particular embodiments, the optical fiber is a fused silica fiber. In a particular embodiment, the fiber cladding and/or the fiber core includes a fraction of fused silica of at least 76 wt %, more preferably of at least 81 wt %, yet more preferably of at least 84 wt %, yet more preferably of at least 88 wt %, yet more preferably of at least 92 wt %, yet more preferably of at least 95 wt %, yet more preferably of at least 97 wt %, most preferably of at least 98 wt %. The higher the fraction of fused silica the better is chemical resistance and temperature resistance.

In one particular embodiment, the core glass has the following features:

The core glass preferably comprises at least 8 wt %, more preferably at least 23 wt %, yet more preferably at least 24 wt %, and most preferably at least 25 wt % or even at least 26 wt % of $SiO_2$. In a particular embodiment, the core glass may even comprise at least 28.3 wt % of $SiO_2$, most preferably at least 34 wt % of $SiO_2$. In some preferred embodiments, the core glass even comprises at least 35 wt % of $SiO_2$, more preferably at least 42 wt %.

Preferred core glasses of the present invention comprise the constituents in the composition ranges as listed below, in percent by weight:

| Component | from | to |
|---|---|---|
| $B_2O_3$ | 0 | 24 |
| $SiO_2$ | 23 | 62.1 |
| $Al_2O_3$ | 0 | 10 |
| $Li_2O$ | 0 | 10 |
| $Na_2O$ | 0 | 18.5 |
| $K_2O$ | 0 | 25.7 |
| BaO | 0 | 57.8 |
| ZnO | 0 | 40 |
| $La_2O_3$ | 0 | 25 |
| $ZrO_2$ | 0 | 10 |
| $HfO_2$ | 0 | 14.2 |
| $SnO_2$ | >0 | 2 |
| MgO | 0 | 8 |
| CaO | 0 | 8 |
| SrO | 0 | 24.4 |
| $Ta_2O_5$ | 0 | 22 |
| $Y_2O_3$ | 0 | 11.9 |
| $Rb_2O$ | 0 | 15 |
| $Cs_2O$ | 0 | 21 |
| $GeO_2$ | 0 | 7.5 |
| F | 0 | 2 |
| Σ $R_2O$ | 5 | 20 |
| Σ MgO, CaO, SrO, ZnO | 20 | 42 |

$R_2O$ is the total of the respective contents of all alkali metal oxides.

One or more of the following components may be contained in the core glass: $Cs_2O$, $Rb_2O$, MgO, CaO, SrO, $Gd_2O_3$, $Lu_2O_3$, $Sc_2O_3$, $Y_2O_3$, $In_2O_3$, $Ga_2O_3$, and $WO_3$.

The following components should preferably not be contained in the core glass or only in concentrations of not more than 500 ppm each, such as caused by unavoidable impurities in the raw materials: $TiO_2$, $CeO_2$, $Nb_2O_5$, $MoO_3$, $Bi_2O_3$, PbO, CdO, $Tl_2O$, $As_2O_3$, $Sb_2O_3$, $SO_3$, $SeO_2$, $TeO_2$, BeO, radioactive elements and coloring components, unless otherwise described in the text. In particular $TiO_2$ should be avoided, since this component may lead to pronounced absorption in the UV range. In preferred embodiments, $WO_3$ is also dispensed with as a constituent.

The components $TiO_2$, $CeO_2$, $Nb_2O_5$, and/or $Bi_2O_3$ may be contained in the core glass in an amount of up to a maximum of 0.5 wt %, preferably up to 0.3 wt %, and most preferably up to 0.2 wt %. In a preferred embodiment, the core glass is free of these components.

The core glass is preferably free of optically active components, in particular $Sm_2O_3$, $Nd_2O_3$, $Dy_2O_3$, $Pr_2O_3$, $Eu_2O_3$, $Yb_2O_3$, $Tb_2O$, $Er_2O_3$, $Tm_2O_3$, and/or $Ho_2O_3$. $CeO_2$ absorbs in the UV range, so that preferred core glasses do not contain any $CeO_2$.

The total content of alkaline earth metal oxide components $La_2O_3$, $Ta_2O_5$, $ZrO_2$, and $HfO_2$ is preferably at least 40 wt %, more preferably at least 42 wt %, yet more preferably at least 50 wt %, and most preferably at least 55 wt %, especially for core glasses with refractive indices of greater than 1.65 wt %. If the content of these components is too low, the preferred refractive index can commonly not be obtained. Depending on the formulation, this total amount should not exceed a value of 72 wt %.

In one specific embodiment, the cladding glass has the following features: The cladding glass preferably has an $SiO_2$ content of >60 wt %, more preferably >65 wt %, and most preferably at least 69 wt %. The $SiO_2$ content is preferably not more than 75 wt % and most preferably not more than 73 wt %. The cladding glass tends to be exposed to stronger environmental impacts than the core glass. A high $SiO_2$ content imparts better chemical resistance. Consequently, the content of this component in the cladding glass is preferably greater than in the core glass.

The composition of the cladding glass is preferably selected or adapted to that of the core glass in such a way that the coefficient of linear thermal expansion of the cladding glass and that of the core glass differ as little as possible. Commonly, the coefficient of thermal expansion (CTE) in a temperature range from 20 to 300° C. may be the same or may be different for the fiber core and the fiber cladding. In particular, the CTE is different. Preferably, the CTE of the cladding is lower than the CTE of the fiber core, typically it is lower by at least $1.0*10^{-6}$/K, but depending on the glass it may typically also be lower by at least $2.5*10^{-6}$/K. The fiber core typically has a CTE from $6.5*10^{-6}$ to $10*10^{-6}$/K, the cladding has a CTE from $4.5*10^{-6}$ to $6*10^{-6}$/K. This ensures that the core of the fiber shrinks more than the fiber cladding upon cooling, so that a compressive stress is built up in the fiber cladding, which protects the fiber, which is beneficial for the mechanical strength of the fiber, in particular its flexural strength.

The table below shows some preferred compositions of cladding glasses that can be used in combination with the core glasses. The cladding glasses comprise (in wt % on an oxide basis):

| Oxide | Group 1 | Group 2 | Group 3 | Group 4 |
|---|---|---|---|---|
| $SiO_2$ | 70-78 | 63-75 | 75-85 | 62-70 |
| $Al_2O_3$ | 5-10 | 1-7 | 1-5 | 1-10 |
| $B_2O_3$ | 5-14 | 0-3 | 10-14 | >15 |
| $Li_2O$ | none | 0-1 | 0-3 | <0.1 |
| $Na_2O$ | 0-10 | 8-20 | 2-8 | 0-10 |
| $K_2O$ | 0-10 | 0-6 | 0-1 | 0-10 |
| MgO | 0-1 | 0-5 | none | 0-5 |
| CaO | 0-2 | 1-9 | none | 0-5 |
| SrO | 0-1 | none | none | 0-5 |
| BaO | 0-1 | 0-5 | none | 0-5 |
| Halogen | none | none | none | None |

In another specific embodiment, the core glass and/or the cladding glass is a chalcogenide glass, which in particular allows applications in the infrared range. The table below shows preferred compositions of chalcogenide core glasses and/or chalcogenide cladding glasses, in mol percent:

| Component | Mol % |
|---|---|
| S | 50-90 |
| Ga | 0-25 |
| As | 0-40 |
| Ge | 0-35 |
| $R^1$ (added in the form of $R^1$Hal) | 0-7.25 |
| $R^2$ (added in the form of $R^2$Hal) | 0-13.5 |
| $M^1$ (added in the form of $M^1Hal_2$) | 0-5 |
| $M^2$ (added in the form of $M^2Hal_2$) | 0-7.25 |
| Ln (added in the form of $LnHal_3$) | 0-4 |
| Total of Ga, As, and Ge | 10-42 |
| Total of $R^1$, $R^2$, $M^1$, $M^2$, and Ln | 0-16 |
| Total of halogens | 0-16 |

Here, Hal=fluorine, chlorine, bromine, and/or iodine; Hal2 and/or Hal3=chlorine and/or bromine; $R^1$=Li, Na, K, Rb, and/or Cs; $R^2$=Ag and/or Cu; $M^1$=Mg, Ca, Sr, and/or Ba; $M^2$=Zn, Cd, Hg, and/or Pb; Ln=La, Ce, Pr, Nd, Pm, Sm Eu, Gd, Tb, Dy, Ho, Er, Tm, Ty, Lu, Y, and Sc.

It is particularly advantageous if the glass fibers, fiber rods, or pressed fiber rods are made of a core glass and cladding glass that are free of Pb and heavy metals. Such fiber systems in particular offer high transmittance in the VIS spectral range and, due to their comparatively high transmittance in the blue spectral range, exhibit high color fidelity, which is particularly important for the medical assessment of tissue. Often only slight differences in color of the tissue decide whether this is a benign or malignant tissue change. It is therefore important to have a high CRI value for the overall system comprising the light source, light guide and imaging device, with CRI (Color Rendering Index) being a key figure of a photometric parameter that describes the quality of color rendering of light sources having the same correlated color temperature. With the glass fibers, fiber rods, or pressed fiber rods described above, a CRI value of >90 can be achieved. Such fiber systems are known from the present Applicant under the name SCHOTT PURAVIS® and have been described with regard to their composition in DE 102012100233 B4 and DE 102013208838 B4. Similar fiber systems which are likewise free of Pb are furthermore described in EP 2072477 B1.

In particular for use in endoscopes it is advantageous if glass fibers, fiber rods, or pressed fiber rods are made of a glass system which has an acceptance angle 2α of greater than 80°, most preferably greater than 100° for the light to be transmitted, which corresponds to a numerical aperture (NA) of greater than 0.64, most preferably greater than 0.77. What can be achieved thereby on the one hand is that in particular light from LEDs, which usually have a very wide emission angle, can be injected into the glass fibers or fiber rods or pressed fiber rods without elevated coupling losses, and this without the need for complex optics at the proximal end. On the other hand, wide-angle illumination can be achieved on the distal end without additional optics, which is most preferably for endoscopic examinations. Optimum illumination over the currently common camera viewing angles (usually 120° diagonally) can be achieved if the glass fibers, fiber rods, or pressed fiber rods have an acceptance angle 2α of at least 120° or an NA of at least 0.86.

Glass fibers as described above usually have a largely undamaged fire-polished surface after their drawing process, which must be protected in the best possible way from being damaged. For this purpose, a so-called sizing is applied to glass fibers prior to the winding process, which protects the fibers especially when the fibers rub against each other, but also when they come into contact with metal surfaces, for example. Such sizing usually consists of wax- or stearin-based solutions that are sprayed onto the glass fibers. Further types of sizing are described in a not yet published application of the present Applicant.

For further mechanical stabilization of the fiber, in particular in the case of fibers with a larger diameter as described above, it has been found to be advantageous if the one or more optical fibers have a polymer-based coating or a protective sheathing made of a polymer-based tube material arranged on their outer surface, at least on parts or sections thereof, for example in the form of a shrink tube. This allows to achieve higher strength and therefore also smaller bending radii of the fibers. The inherent drawback of a thicker fiber in terms of increasing rigidity and an increase in the minimum permissible bending radius can be significantly reduced or compensated for with this measure.

According to one embodiment, the light guide comprises a plurality of optical fibers, and at least one optical fiber, preferably a plurality of optical fibers, most preferably all optical fibers have a polymer-based coating or a protective sheathing made of a polymer-based flexible tube material arranged on their outer surface, at least partially and/or in sections thereof.

Preferable coatings include coatings made of a compound selected from the group consisting of acrylates, polyamides, polyurethanes, polyimides, epoxy, ethylene-tetrafluoroethylene copolymers, and poly-xylene-based compounds (also referred to as poly-xylylene-based coatings), for example based on poly-para-xylene compounds, also known as a coating material under the trade name "Parylene", for example, or mixtures of these compounds. Suitable coating materials are available, for example, under the trade names or brands or designations NYLON® (polyamide) or TEFZEL® or Parylene® or PMMA (polymethyl methacrylate) as coatings or coating materials. Such layers are usually cured by heating or by UV light. Alternatively or additionally, the coating may also comprise thermoplastic elastomers, for example a thermoplastic polyester elastomer or a thermoplastic copolyester elastomer as is commercially available under the trade name Hytrel, for example, or a silicone.

In special cases, metallic coatings may also be used, for example made of gold or aluminum.

Particularly advantageously, such a coating is or can be applied to the one or more optical fibers by dip-coating, spray-coating, extrusion, or deposition at low pressure immediately after the fibers have been drawn. In particular, such a coating can be applied to the one or more optical fibers by dip-coating, spray-coating, extrusion, or deposition at low pressure immediately after the fibers have been drawn, for example. An application immediately after the fiber or fibers have been drawn in particular allows to achieve that the virtually perfect fire-polished surface of the fiber(s) is preserved before it comes into contact with other materials or with other fibers. This permits to at least mitigate micro-damage that reduces the strength of the fiber(s). Moreover, it is even conceivable, in principle, that such a coating can also lead to the healing of any previous damage or can at least partially mitigate the effect of such previous damage. Protection against hydrolytic attack can also be achieved.

Such layers are usually applied by pulling the freshly drawn light guide in the form of a fiber through a pot with a nozzle, which holds the polymer material the coating is produced of, and the nozzle is also used to adjust the layer thickness, inter alia.

The layer thickness of this coating is typically in a range from 5 µm to 100 µm, preferably in the range from 10 µm to 50 µm.

Furthermore, an additional organic coating may be applied in addition to this first coating. Such additional coatings are also referred to as buffer coatings and are usually used for quartz fibers. Materials that may be considered for such buffer coatings include PMMA, polyamide (NYLON®), polyimide, or fluorinated polymers such as an ethylene-tetrafluoroethylene copolymer (ETFE for short), which is commercially available under the trade name TEFZEL®, for example. Such a further coating serves to increase the robustness in terms of flexural strength. This buffer layer may in particular also comprise a thermoplastic elastomer, for example a thermoplastic polyester elastomer or a thermoplastic copolyester elastomer, such as commercially available under the trade name Hytrel®, for example, and/or polyvinylidene fluoride, for example available under the trade name Kynar, or polytetrafluoroethylene (e.g. available under the trade name Teflon), or polyurethane. Such buffer coatings may be applied by spray-coating, dip-coating, extrusion, and electrostatic techniques, for example.

Such a layer system may consist, for example, of a two-layer system in which a comparatively thin layer, typically 10 µm to 50 µm in thickness and made of an acrylate or epoxy compound, for example, is applied to the light guide, and then a so-called buffer layer, e.g. NYLON®, TEFZEL®, PMMA, or polyimide, is applied as a further mechanical protection, which will then have a significantly greater wall thickness of typically 50 µm up to 200 µm.

For applications with very little space, the first coating will be sufficient to ensure a flexural strength as high as possible.

It should be noted here that other methods are also conceivable, in particular to increase the strength of the fiber. For example, selective heat treatment processes similar to the thermal toughening of glass could be employed to produce a higher compressive stress close to the surface, which can increase the flexural strength of the fiber. Chemical toughening of the fiber is also conceivable. However, in order to maintain the optical properties of the fiber, an additional jacket would be necessary, so that a selective additional compressive stress can be produced in this additional jacket by ion exchange in a molten salt or by spray-coating a salt layer with subsequent heat treatment. Electron beam or ion beam toughening is also conceivable. However, the latter of these processes are comparatively complex. Moreover, they make it difficult to retain the optical properties of the fibers.

According to a further embodiment, the coating may also be designed to be light-blocking, i.e. opaque, or light-absorbing, e.g. colored, such as black or blue. This is advantageous because it allows to reduce crosstalk to the camera chip.

An embodiment in which the light guide comprises at least one glass fiber, in particular a glass fiber comprising a multi-component silicate glass or a glass fiber made of a multi-component silicate glass, or preferably a glass fiber bundle which in particular is in the form of a glass fiber bundle comprising glass fibers comprising a multicomponent silicate glass or made of a multicomponent silicate glass or consisting of glass fibers made of a multicomponent silicate glass is particularly advantageous. This is because the optical properties of the glass fiber bundle and therefore of the light guide or of the diagnostic, surgical, and/or therapeutic device can be adapted particularly flexibly with such glass fibers. Furthermore, such light guides which are based on glass optical fibers, exhibit significantly higher temperature resistance than a polymer optical fiber (POF). This is in particular relevant if particularly good coupling efficiency is sought to be achieved and, for example, a thin fiber bundle made of or comprising glass optical fibers is directly contacted on an LED chip or arranged very close to such a chip. However, a polymer optical fiber or a fiber bundle composed of or comprising polymer optical fibers would not withstand such a thermal load, rather the fibers would melt.

According to one embodiment, the one optical fiber or the plurality of optical fibers are enclosed in an injection ferrule at the proximal end, which is designed as a mechanical interface to the laser light source and thus allows for a defined injection of light in terms of focus distance and centering relative to the light source. In the case of a single fiber or a plurality of individual fibers, ideally three or seven individual fibers, the injection ferrules may be provided in the form of so-called SMA connectors which in particular allow for defined alignment with the laser light source and are in particular also used for laser applications. So-called FC connectors are also conceivable for this purpose. Here, again, an arrangement of seven individual fibers is particularly advantageous, since this allows for a substantially circular cross-section on the one hand, and on the other for a minimized gusset area between the individual fibers. This has advantages in terms of coupling efficiency. Gusset refers to the interspaces in between a bundle of circular fibers. A further optimal fiber arrangement would result with 19 individual fibers, in which case the individual fibers are then optimally tightly packed in two shells around a central fiber. The individual fibers are usually fixed in place by an adhesive, e.g. a two-component hot-curing epoxy adhesive, or a UV-curing adhesive.

In order to increase coupling efficiency, provision may also be made for the optical fibers to be provided in a hot-fused fashion at the proximal end. On the one hand, this allows to minimize gusset areas, since the hot deformation process deforms the per se round individual fibers so as to assume an at least approximately hexagonal cross-sectional shape, so they can be arranged almost without gaps. Moreover, more fibers can be accommodated for a given coupling cross-sectional area or focus diameter, so that a higher luminous flux can be transmitted.

It is possible for such hot-fused fibers to be accommodated in an injection ferrule at the proximal end, for example. However, it is also possible for the hot-fused fibers to be provided without a ferrule at the proximal end. This is particularly advantageous for embodiments which require efficient use of space, for example in the case of particularly small cross section areas at the proximal end, or the like.

According to a further embodiment, the at least one optical fiber and/or the plurality of optical fibers and/or the light guide is deformed at the distal end compared to the proximal end. This means that, according to one embodiment, the at least one optical fiber and/or the plurality of optical fibers and/or even the light guide itself may have a cross-sectional area with a shape that is different at the distal end from that at the proximal end. For example, it is possible that the cross-sectional area of the one fiber and/or of the plurality of fibers and/or of the light guide is substantially circular at the proximal end, i.e. within measurement accuracy, but is oval or kidney-shaped or substantially D-shaped at the distal end, for example. It is also possible that different optical fibers have different cross-sectional shapes, more particularly the cross-sectional shape may be circular at the proximal end, but may be oval for one or more fibers and kidney-shaped for others at the distal end. Other cross-sectional shapes are also conceivable, for example rectangular or approximately rectangular cross-sectional shapes, in particular at the distal end, or, more generally, polygonal cross-sectional shapes. It is furthermore possible for the cross-sectional area of the one fiber and/or else of the plurality of fibers and/or of the light guide at the proximal and/or distal end to be delimited by at least two lines which have radii of curvature different from one another and/or which have the shape of a differential area of two only partially overlapping circles and/or ellipses. In particular, the cross-sectional area may have the shape of a circular segment, and for the case of a circular segment one of those radii of curvature is infinite, i.e. defining a straight line within measurement accuracy. Such a cross-sectional area in the form of a circular segment may also be referred to as a D-shaped cross-sectional area or a substantially D-shaped cross-sectional area.

In particular an approximately D-shaped cross section provides for excellent exploitation of the available cavities, here, and can thus result in an increased luminous flux or increased illuminance at the distal end of the endoscope. In the context of the present disclosure, an essentially D-shaped cross section or an essentially D-shaped cross-sectional area is understood to mean in particular an area having a circular segment shape.

Such a configuration may in particular be advantageous to ensure a particularly favorable spatial arrangement of the fiber and/or the fibers and/or of the light guide with respect to the camera chip.

More generally, it is possible for the at least one optical fiber and/or the optical fibers to have a cross-sectional shape different from a circular one, at least within measurement accuracy, at least in sections thereof. This may be advantageous in order to provide for particularly efficient, for example space-saving arrangements of individual elements in the second component of the endoscope.

This can be advantageous especially at the distal end of the light guide.

Therefore, according to one embodiment, the at least one optical fiber and/or the plurality of optical fibers has/have a flattened cross-sectional shape with an aspect ratio of at least 1.5:1 at least at the distal end of the light guide, and/or an oval cross section and/or a kidney-shaped cross-section, and/or a cross-sectional area that is delimited by at least two lines which have radii of curvature different from one another and/or which have the shape of a differential area of two only partially overlapping circles and/or ellipses.

According to a further embodiment, the numerical aperture of the one or more optical fibers is at least 0.7, preferably at least 0.8, and most preferably at least 0.85. The core of the one or more optical fibers preferably comprises a glassy material with a composition that is selected from the glass compositions and glass composition ranges for core glasses listed above. In particular, the core of the glass fiber may predominantly comprise such a glassy material, that is to say at least 50 wt %, or essentially, i.e. at least 90 wt %, or even may completely be made thereof.

An embodiment in which the core of the one or more optical fibers comprises such a glassy material is advantageous because in this way it is possible to achieve very good illumination of the camera's field of view (here in particular for 1×1 mm$^2$ area CMOS cameras, for example).

According to a further embodiment, the one optical fiber or the plurality of optical fibers are designed such that the core and/or cladding glasses of the one optical fiber or of the plurality of optical fibers is free of lead and/or other heavy metals, and also free of antimony and/or arsenic and/or other critical elements such as Cr(VI), except for unavoidable traces.

In a further aspect, the present invention relates to a disposable endoscope system comprising a first component and second components that are individually packaged in a sterile manner and which preferably are or can be in the form of shafts that, once removed from their sterile package, can be detachably coupled with the first component in order to obtain an endoscope, in particular an endoscope according to embodiments of the present disclosure.

In the context of the present disclosure, shaft refers to a second component of an endoscope, which has only a small cross-sectional area compared to its length. In other words, the shaft is thin compared to its length. Such a configuration of a second component in the form of a shaft is advantageous, especially when areas that are only very difficult to access are examined using the endoscope, and/or for applications in medical technology.

One advantage of the endoscope system according to the present disclosure is to have second components available, in particular shafts, that are already packaged in a sterile manner, for examinations in quick succession so that several areas can be examined quickly, or so that in the case of medical examinations several brief examinations of different patients can be carried out one after the other while ensuring adequate hygiene. Therefore, it is especially advantageous for the endoscope system according to the present disclosure that the second components can be coupled to the first component in a detachable manner in order to provide the advantages of a single-use endoscope, while at the same time the parts of the endoscope system which do not necessarily have to be sterilized in the case of medical examinations or for other medical purposes, for example, are accommodated in a first component that can be used repeatedly. In this way it is possible, for example, to provide illumination with laser light even for disposable endoscopes.

According to one embodiment, the second component is provided in the form of an at least partially flexible shaft which has a flexible sheathing comprising a flexible tube or braided tube or shrink tube, which encloses the light guide with its at least one optical fiber, at least in sections thereof, as well as a power supply line for electrically powering the camera chip and preferably at least one signal return line to a data and/or image processing unit that may in particular be provided as part of the first component. Such a configuration, in particular with a flexible shaft, is particularly suitable for medical applications.

According to a further embodiment, the second component is in the form of a shaft that is rigid at least in sections thereof, which has a rigid sheathing comprising a shell enclosing the light guide with its at least one optical fiber as well as a power supply line for electrically powering the camera chip and preferably at least one signal return line, preferably to a data and/or image processing unit that may in particular be provided as part of the first component. Such a configuration may be particularly advantageous since this allows to better protect the elements forming part of the second component, here in the form of a rigid shaft, against mechanical impacts.

In yet another aspect, the present disclosure relates to a light source for an endoscope, in particular a light source for an endoscope according to embodiments of the present disclosure. The light source for an endoscope, in particular for an endoscope according to embodiments of the present disclosure, comprises a laser for emitting primary light, preferably for emitting blue and/or ultraviolet light, and at least one converter associated with the laser, and a light guide comprising one or more optical fibers, wherein the laser is arranged so that the light from the laser is incident on at least a portion of a surface of the converter and so that the proximal end of the light guide with its at least one optical fiber receives the converted and/or scattered and/or emitted light from the converter.

Such an embodiment of a light source provides improved coupling efficiency, since it allows to use one optical fiber or a plurality of optical fibers with a high numerical aperture in air, for example. Also, the excitation laser can be spatially decoupled from other elements of the endoscope in this way so that, moreover, excessive heating of these elements by the laser can be prevented, for example.

More generally, without being limited to the example described above, it is furthermore possible for the light source to comprise further constituents or components. The light source may in particular comprise optical elements that are able to direct and/or modify laser light, for example, in particular to collimate the laser light. For example, such components may be provided in the form of diffractive optical elements (DOE). Such an embodiment may be advantageous, for example, if the DOE is configured so as to completely illuminate at least one surface of the converter, or so as to direct the light from the laser onto a plurality of different converters or converter elements. However, it is also possible to provide optical elements that do not collimate and/or direct and/or modify the primary light, but rather optical elements which direct and/or modify and/or collimate the secondary light, i.e. the converted and/or scattered light.

In particular a diffuser can be provided at the distal end, which emits the light conducted by the fiber in a wider solid angle and thus allows to illuminate a larger tissue area.

According to a further embodiment, the light source comprises an optical fiber for feeding the laser light to the converter, with the emission end of the optical fiber and the injection end of the light guide facing the same surface of the converter so that the converter is operated in remission and the direction of light conduction for conducting the laser light in the optical fiber is opposite to the direction of conduction of the light injected into the light guide from the converter. In this way, direct laser light can be prevented from being injected into the light guide of the endoscope, which is advantageous from a safety point of view. In particular in the event of a malfunction of the converter, such an arrangement is able to prevent the very intense laser light or primary radiation from the laser light source from reaching the patient's tissue directly. It should be noted that the converters in this arrangement are usually coupled to a heat sink in a thermally conductive way, e.g. in the form of a heat sink as a passive component or with active cooling. In addition, this heat sink is also designed as a so-called beam trap, for the event the converter should be damaged or even completely destroyed.

According to a further embodiment, the converter comprises two converter elements, the converter elements each comprising a ceramic converter material, and preferably the converter elements comprise different converter materials so that the converter elements convert the laser light into light of different spectral composition, and at least one laser is provided for irradiating a respective laser beam onto the two converter elements.

Also conceivable are individual converters consisting of a mixture of two converter materials which emit light with different wavelengths.

Such embodiments allow to obtain a particularly good CRI, meaning they allow to reproduce colors particularly well.

The light guide preferably has two injection ends, and the converter elements are arranged in such a way that the light emitted by the converter elements is injected into a respective one of the injection ends.

More generally, the light source may be configured so as to comprise a plurality of converter elements, and the light guide is then configured so as to comprise a plurality of injection ends, the converter elements are arranged so that the light emitted by each of the converter elements is injected into a respective one of the injection ends, with the number of converter elements corresponding to the number of injection ends, so that preferably each converter element has a separate injection end associated therewith.

Such embodiments allow to achieve particularly high CRI values. This is because with the optical fibers color mixing is actually additive.

It may be particularly advantageous if the ratio of the luminous fluxes injected into the light guide can be adjusted. This allows to adapt the color coordinates of the light generated by the light source in a particularly straightforward manner. Therefore, according to one embodiment, the light source comprises a device for adjusting the ratio of the light fluxes injected into the light guide by the two converter elements or by all the converter elements the light source consists of.

BRIEF DESCRIPTION OF THE DRAWINGS

The invention will now be explained in more detail with reference to figures in which the same reference numerals designate the same or equivalent elements, and wherein:

FIGS. 3 and 4 are schematic views of parts of light sources according to embodiments, not drawn to scale.

DETAILED DESCRIPTION

Figure 1:
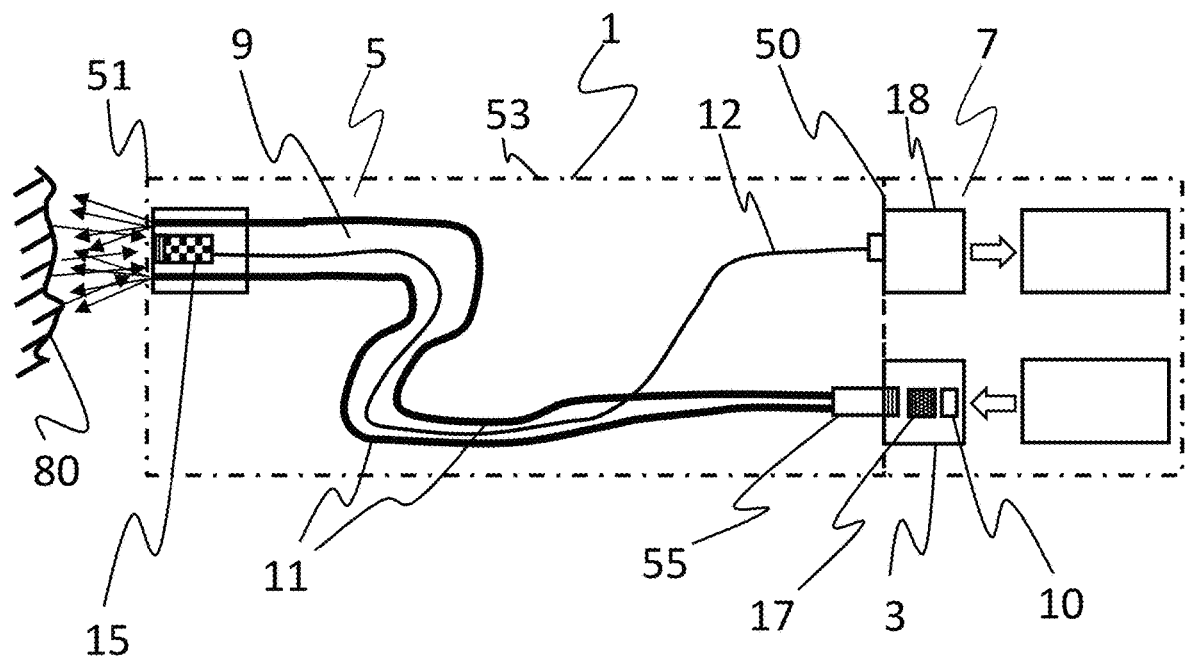
FIG. 1 shows a schematic view of an endoscope according to one embodiment, not drawn to scale.

FIG. 1 is a schematic view of an endoscope 1 according to one embodiment, not drawn to scale. Endoscope 1 comprises a first component 7 and a second component 5, with the first component being shown on the right in the view, and the second component 5 on the left. The second component 5 has a proximal end 50 coupled to the first component 7. Provision may be made for the proximal end 50 of the second component 5 coupled to the first component 7 so as to be detachable. Thus, more particularly, the two components 5 and 7 may be provided in a form so as to be releasably coupled. This can be particularly advantageous if one component is only intended for single use, and if the other component, for example the first component 7 in the present case, comprises parts that are intended for multiple use, in particular high quality and/or expensive parts. This may in particular be the case if one of the components, here for example the first component 7, comprises a special light source such as a light source comprising at least one laser.

The second component furthermore has a distal end 51 with a camera chip 15 disposed at the distal end 51, for capturing images. Furthermore, the second component 5 includes a light guide 9 extending therethrough and comprising at least one optical fiber 11, which is designed to conduct light of a light source 3 from the proximal end 50 to the distal end 51 of the light guide 9 and to emit it at the distal end 51. Furthermore, a power supply line (not shown) for electrically powering the camera chip 15 extends through the second component 5.

Light source 3 comprises at least one laser 10 that is designed to emit primary light, and a converter 17 which at least partially converts the light from laser 10 into light of a different wavelength and emits it. The converter 17 is coupled to the proximal end 50 of the second component 5 coupled to the first component 7 such that the light converted and emitted by the converter 17 is injected into the light guide 9.

The converter 17 preferably comprises a ceramic converter material.

Converter 17 may be configured so as to comprise at least two ceramic converter materials which convert the light from laser 10 (or the laser light) into light of different spectral compositions.

More generally, without being limited to the endoscope 1 as shown in FIG. 1 by way of example or to the light source 3 comprising the laser 10 forming part of the endoscope 1 according to FIG. 1 by way of example, the converter 17 can be understood as comprising a converter element (not shown here), which comprises the converter material. This converter element may in particular be designed so as to comprises the converter material, which may most preferably be made of or comprise a ceramic material, for example, that is applied on a base, for example in the form of a thin material layer, which base may be effective as a diverter of thermal energy that is resulting from the conversion of the primary light. Such a configuration is particularly preferred when the light source or the converter is operated in remission.

According to one embodiment of the endoscope, the converter 17 is optically coupled to the light guide 9 in such a way that light remitted by the converter 17 is and/or can be injected into the light guide 9. The laser 10 can preferably be arranged and oriented towards the converter 17 such that only light converted and/or scattered by the converter 17 is and/or at least can be injected into the light guide 9. Such a configuration is particularly useful from a safety point of view if it is intended to prevent high-energy laser light from reaching a tissue surface 80, for example, which is shown on the left here in FIG. 1 by way of example.

Advantageously, provisions may be made for the laser 10 to be arranged in such a way that the light of laser 10 is and/or can be directed onto the converter 17 in a direction opposite to the light emission direction of the light converted by the converter 17 and injected into the light guide 9.

In particular under assembly considerations, especially if the second component 5 is only intended for single use, it may be advantageous if the light guide 9 comprises not more than ten optical fibers 11. However, more generally, it is also possible that a light guide 9 comprises up to a few hundred individual fibers 11, this being dependent on the respective fiber diameters and the resulting or addressed thickness of the fiber bundle and hence of the light guide 9, and the number of fibers 11 can be chosen accordingly.

Typical fiber diameters (or fiber thicknesses) of optical fibers 11 can preferably range from 100 µm to 1000 µm, more preferably up to 600 µm, most preferably the maximum fiber diameter is in a range from 150 µm to 400 µm. However, thinner fibers with diameters of 30 µm, 50 µm or 70 µm are also conceivable.

According to one embodiment, the one optical fiber 11 or the plurality of optical fibers 11 is/are in the form of step-index glass fibers.

The one optical fiber 11 and/or the plurality of optical fibers 11 may preferably be designed such that the numerical aperture (NA) in air of the at least one fiber 11 and/or the plurality of optical fibers 11 is at least 0.7, preferably at least 0.8, and most preferably at least 0.85. This is particularly beneficial for achieving a high CRI (Color Rendering Index).

In particular under assembly considerations it may be advantageous if the at least one optical fiber 11 or the plurality of optical fibers 11 are arranged in an injection ferrule 55 at the proximal end 50 of light guide 9, as shown schematically in FIG. 1.

The second component 5 may be provided in the form of a shaft that is flexible at least in sections thereof, for example, or else as a shaft that is rigid at least in sections thereof. The second component may for instance comprise a sheathing 53, as shown in FIG. 1 by way of example. In the case where the component 5 is provided in the form of a shaft that is flexible at least in sections thereof, the sheathing 53 is designed to be flexible, in particular in the form of a flexible tube, braided tube, or shrink tube. In the case where the component 5 is provided in the form of a shaft that is rigid at least in sections thereof, the sheathing 53 is preferably rigid and comprises a shell. More generally, without being limited to the example shown by way of example here, the sheathing 53 encloses at least sections of the light guide 9 comprising the at least one fiber 11, and a power supply line for electrically powering the camera chip 15 and preferably at least one signal return line 12, preferably a line to a data and/or image processing unit 18 that may in particular be provided as part of the first component 7.

A particularly preferred exemplary embodiment has been found to be an assembly comprising seven optical fibers 11 of approximately 200 µm in thickness, which are designed as what is known as a wide-angle fiber with an NA>0.85, and the seven optical fibers 11 are arranged around the camera chip 15, and at the proximal end they are glued into a common injection ferrule 55. Alternatively, these seven optical fibers 11 may also be hot-fused into the injection ferrule 55. More generally, however, it is also possible and may even be preferred for hot-fused fibers to be provided without a ferrule at the proximal end.

FIGS. 2*a*-2*e* schematically shows views of distal ends 51 of a second component 5 of an endoscope 1, which are not drawn to scale. In each case, distal end 51 comprises the light guide 9 which comprises a plurality of fibers 11 here in each case, and a camera chip 15.

Figures 2A, 2B, 2C, 2D, 2E:
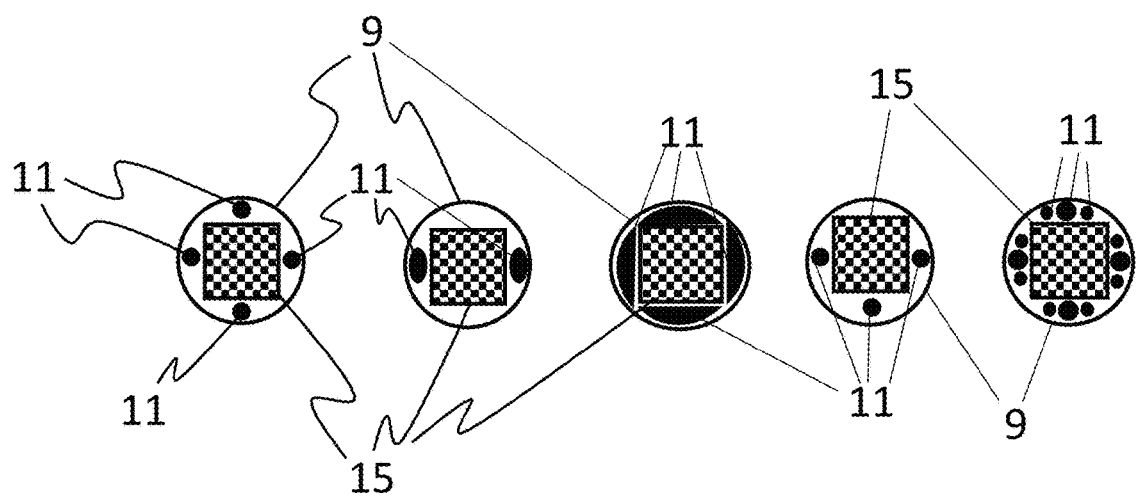
FIGS. 2a-2e show schematic views of distal ends of an endoscope, not drawn to scale.

In FIG. 2a, four fibers 11 are provided, each having a circular cross section within measurement accuracy. Here, these fibers are arranged around the camera chip 15 which has an approximately square shape in this case by way of example, and this in such a way that one fiber 11 is arranged on each respective side of the camera chip 15. In FIG. 2d, by contrast, fibers 11 are only arranged on three sides of the camera chip 15.

In FIG. 2b, only two fibers 11 are arranged on two sides of the camera chip 15. Here, the cross section of the optical fibers 11 is not circular, but rather oval or elliptical. The optical fibers 11 may in particular be formed so as to be deformed on the distal end 51 opposite to the proximal end 50—not shown here. It is in particular possible for the optical fibers 11 to have a circular cross section at the proximal end 50, but to be deformed at the distal end, as in the present example. This may be advantageous for arranging the fibers 11 around the camera chip.

The optical fibers 11 and/or the at least one optical fiber 11 may preferably have a flattened cross-sectional shape, at least at the distal end 51 as shown here by way of example, in particular with an aspect ratio of at least 1.5:1, and/or an oval cross-sectional shape, and/or a kidney-shaped cross section. Although other cross-sectional shapes such as polygons are conceivable, flattened shapes are just particularly advantageous with regard to the arrangement of the optical fibers 11 around the camera chip 15. FIG. 2c shows an arrangement in which four fibers are arranged around the camera chip 15, which have a substantially D-shaped cross section at their distal ends.

The distal ends of the fibers 11 shown in FIG. 2b as well as in FIG. 2c may be deformed in the illustrated manner, for example by a hot forming process, so that the corresponding cross-sectional areas or cross-sectional shapes as shown in FIGS. 2a to 2d are formed. To this end, the fiber 11 is heated in a mold to above its working temperature and is then deformed under pressure. Due to the viscosity of the fiber material, it is of course impossible to reproduce perfect geometries. A substantially D-shaped cross section will therefore have minor chamfers at the tapering corners. In principle, such a shaping process can be used for glass fibers, quartz fibers or else for plastic fibers, while the deformation temperature has to be adapted to the respective material. For plastic optical fibers (POFs) it will typically be between 150° C. and 300° C., for glass optical fibers typically between 500° C. and 800° C., depending on the type of glass, and for fused silica optical fibers up to 2000° C.

FIG. 2e shows a 12-fiber arrangement, as already described above. Here, a total of four thicker fibers 11 and eight thinner fibers are grouped in such a way that in each cavity (segment) the thick fiber 11 is arranged in the center of the cavity and the two thinner fibers 11 are arranged to the right and left of the thick fiber 11. Despite the fairly few fibers 11, the cavity space is very well exploited in this way, so that a comparatively high luminous flux can be achieved. Such examples may be expanded to a 20-fiber arrangement comprising 20 individual fibers 11, i.e. 5 fibers 11 in each cavity, ideally with 3 graduations in diameter for the fibers 11 in this case.

Finally, FIGS. 3 and 4 show two schematic views of a section or portion of a light source 3, not drawn to scale.

The light source 3 for an endoscope 1, in particular for an endoscope according to the present disclosure, comprises a laser 10 (not shown) for emitting primary light, preferably for emitting blue and/or ultraviolet light, and at least one converter 17 associated with the laser, and a light guide 90. Here, the converter 17 is designed so as to comprise a first converter element 170 comprising a ceramic converter material 173. Converter element 170 is configured such that the ceramic converter material 173 is provided as a material layer on a base or heat sink 172 that forms part of the converter element and may be adapted to dissipate thermal energy generated by the conversion of the laser light, for example. Furthermore, a light guide 90 is provided, which comprises one or more optical fibers 11. Laser 10 (not shown) is arranged such that the light from laser 10 is incident on at least a portion of a surface of the converter 17, namely in particular the surface 175 that is at least partially made of the converter material 173, and so that the proximal end of the light guide comprising the at least one optical fiber 11 receives the light converted and/or scattered and/or emitted by the converter 17.

According to the view in FIG. 3, provisions may be made for feeding the laser light to the converter 17 by an optical fiber 100. In this case, the emission end of optical fiber 100 and the injection end 91 of the light guide 90 preferably face the same surface 175 of the converter 17, as shown in FIG. 3 by way of example, so that the converter is operated in remission. In this case, the direction of light conduction in optical fiber 100 is opposite to the conduction direction of the light injected into the light guide 90 from the converter. Advantageously, the distal end 93 of light guide 90 may be provided with an interface to the light guide 9 of the second component 5 of an endoscope. Light source 3 may furthermore comprise optical elements, as shown here in the form of a lens 96, for example for beam shaping and/or focusing and/or collimation purposes, in particular so-called diffractive optical elements.

FIG. 4 shows a further view of a section or part of a light source 3 comprising a laser 10, not illustrated here. Here, converter 17 comprises two converter elements 170, 171. Converter element 170 comprises a first converter material 173, in particular a ceramic converter material 173, and converter element 171 comprises a second converter material 174, in particular a ceramic converter material 174, and the converter materials 173 and 174 are designed to be different so that the converter elements 170 and 171 convert the laser light into light of different spectral composition. For example, converter material 173 may be provided as a so-called "red phosphor", and converter material 174 as a so-called "yellow phosphor". Such a configuration is particularly advantageous in order to optimize the so-called CRI, in particular in order to achieve a CRI of more than 80.

More generally, the light source 3 may comprise a plurality of converter elements 170, 171, in which case the number of injection ends 91, 92 of the light guide 90 preferably corresponds to the number of converter elements.

In particular, at least one optical fiber 100 is provided, which directs the light from laser 10 onto the surface 175 of the converter elements 170, 171. In this respect, the number of optical fibers 100 preferably corresponds to the number of converter elements 170, 171, as illustrated here for two converter elements by way of example. Also shown is the distal end 93 of light guide 90, which may preferably be provided with an interface to the light guide 9 of the second component 5.

LIST OF REFERENCE NUMERALS

1 Endoscope
3 Light source

5 Second component of endoscope, e.g. shaft 17 Converter
50 Proximal end of second component
51 Distal end of second component
53 Sheathing
55 Injection ferrule
7 First component of endoscope
9,90 Light guide
91,92 Injection ends of light guide 90
93 Distal end of light guide 90, interface
96 Optical element, e.g. lens
10 Laser
11,100 Optical fiber
12 Signal return line
15 Camera chip
170,171 Converter element
172 Heat Sink
173,174 Converter material
175 Surface area of converter
18 Data and/or image processing unit

What is claimed is:

1. An endoscope, comprising:
a first component;
a second component having a proximal end and a distal end, the proximal end being coupled to the first component;
a light source integrated in the first component, light source comprising at least one laser and a converter, the at least one laser emits primary light, the converter converts the primary light at least partially into secondary light, the secondary light having a different wavelength than the primary light;
an image capturing element arranged at the distal end; and
a light guide comprising at least one optical fiber extending through the second component,
wherein the converter is coupled to the proximal end such that the primary and secondary light is injected into the light guide so that the at least one optical fiber conducts the primary and secondary light from the proximal end to the distal end and emits the primary and secondary light at the distal end, and
wherein the at least one optical fiber comprises a step-index glass optical fiber, and wherein the step-index glass optical fiber comprising a glass composition that is free, except for unavoidable traces, of a material selected from a group consisting of lead, heavy metals, antimony, arsenic, Cr(VI), and any combinations thereof.

2. The endoscope of claim 1, wherein the proximal end is removably coupled to the first component.

3. The endoscope of claim 1, wherein the image capturing element is a camera chip or a fiber optic element.

4. The endoscope of claim 3, further comprising a power supply line electrically powering the camera chip.

5. The endoscope of claim 1, wherein the converter comprises a ceramic converter material.

6. The endoscope of claim 1, wherein the converter comprises at least two ceramic converter materials that convert the primary light into light of different spectral compositions.

7. The endoscope of claim 6, wherein the converter comprises two converter elements each comprising a different one of the at least two ceramic converter materials.

8. The endoscope of claim 7, further comprising a device for adjusting a ratio of light fluxes injected into the light guide from the two converter elements.

9. The endoscope of claim 1, wherein the converter is optically coupled to the light guide so that the primary and secondary light remitted by the converter is injected into the light guide.

10. The endoscope of claim 1, wherein the at least one laser is arranged and oriented so as to face the converter such that only the primary and secondary light is injected into the light guide.

11. The endoscope of claim 1, wherein the at least one laser is arranged so that the primary light is directed onto the converter substantially opposite to the light emission direction of the secondary light converted by the converter and injected into the light guide.

12. The endoscope of claim 1, wherein the at least one optical fiber comprises not more than twenty optical fibers, and wherein the not more than twenty optical fibers have a diameter ranging from 100 µm to 1000 µm.

13. The endoscope of claim 1, wherein the at least one optical fiber has a numerical aperture (NA) in air of at least 0.7.

14. The endoscope of claim 1, wherein the at least one optical fiber comprises an outer surface having a coating or sheathing made of a polymer-based material, the coating or sheathing having a thickness from 10 µm to 100 µm.

15. The endoscope of claim 14, wherein the polymer-based material is a compound selected from a group consisting of acrylate, polyamide, polyurethane, polyimide, epoxy, ethylene, tetrafluoroethylene copolymer, poly-xylene, and any mixtures thereof.

16. The endoscope of claim 14, further comprising an outer coating on the coating or sheathing, the outer coating comprising a compound selected from a group consisting of PMMA, polyamide, polyimide, fluorinated polymer, ethylene-tetrafluoroethylene copolymer, and any mixtures thereof.

17. The endoscope of claim 1, wherein the at least one optical fiber is disposed in an injection ferrule at the proximal end or is hot-fused at the proximal end.

18. The endoscope of claim 1, wherein the at least one optical fiber and/or the light guide is deformed at the distal end compared to the proximal end.

19. The endoscope of claim 1, wherein the at least one optical fiber has a flattened cross-sectional shape with an aspect ratio of at least 1.5:1 at least at the distal end.

20. The endoscope of claim 19, wherein the flattened cross-sectional shape is a shape selected from a group consisting of oval, kidney-shaped, and circular segment-shaped.

21. The endoscope of claim 1, wherein the proximal end is uncoupled from, but removably couplable to the first component, wherein the first component and the second components are individually packaged in a sterile manner.

22. The endoscope of claim 21, wherein the second component comprises a sheathing and a power supply line, the sheathing enclosing the light guide and the power supply line, the power supply line being connected to the image capturing element.

23. The endoscope of claim 22, wherein the second component further comprises at least one signal return line, the sheathing enclosing the at least one signal return line.

24. The endoscope of claim 23, wherein the first component further comprises a data and/or image processing unit, the at least one signal return line being removably couplable to the data and/or image processing unit.

25. The endoscope of claim 1, wherein the at least one laser emits the primary light as blue light and/or ultraviolet light.

* * * * *